US009273078B2

(12) United States Patent
Ziegler et al.

(10) Patent No.: US 9,273,078 B2
(45) Date of Patent: Mar. 1, 2016

(54) HALF-PHTHALOCYANINE-LIKE CHELATES AND SYNTHESIS THEREOF

(71) Applicants: Christopher J. Ziegler, Copley, OH (US); Laura Crandall, Barberton, OH (US); Richard S. Herrick, Worcester, MA (US)

(72) Inventors: Christopher J. Ziegler, Copley, OH (US); Laura Crandall, Barberton, OH (US); Richard S. Herrick, Worcester, MA (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 14/561,955

(22) Filed: Dec. 5, 2014

(65) Prior Publication Data
US 2015/0203520 A1 Jul. 23, 2015

Related U.S. Application Data

(60) Provisional application No. 61/912,208, filed on Dec. 5, 2013.

(51) Int. Cl.
*C07F 5/02* (2006.01)
*C07F 15/06* (2006.01)
*C07F 5/00* (2006.01)
*C07F 9/6521* (2006.01)
*C07F 13/00* (2006.01)

(52) U.S. Cl.
CPC . *C07F 13/00* (2013.01); *C07F 5/02* (2013.01); *C07F 9/65211* (2013.01); *C07F 15/06* (2013.01)

(58) Field of Classification Search
None
See application file for complete search history.

(56) References Cited

U.S. PATENT DOCUMENTS

| 4,774,339 | A | 9/1988 | Haugland et al. |
| 5,189,029 | A | 2/1993 | Boyer et al. |
| 5,433,896 | A | 7/1995 | Kang et al. |
| 5,463,044 | A | 10/1995 | Nukada et al. |
| 5,498,641 | A | 3/1996 | Urano et al. |
| 5,728,529 | A | 3/1998 | Metzker et al. |
| 5,804,395 | A | 9/1998 | Schade et al. |
| 5,861,287 | A | 1/1999 | Metzker et al. |
| 5,994,063 | A | 11/1999 | Metzker et al. |
| 6,005,113 | A | 12/1999 | Wu et al. |
| 6,340,750 | B1 | 1/2002 | Burgess et al. |
| 8,426,850 | B2 | 4/2013 | Gresser et al. |

FOREIGN PATENT DOCUMENTS

| EP | 361936 A2 | 4/1990 |
| WO | WO9419355 | 9/1994 |
| WO | WO02057479 | 7/2002 |
| WO | WO03066812 | 8/2003 |
| WO | WO2010051530 | 5/2010 |
| WO | 2015/077427 A1 | 5/2015 |

OTHER PUBLICATIONS

Loudet, A. et al., "BODIPY Dyes and Their Derivatives: Syntheses and Spectroscopic Properties," Chem. Rev. 2007, 107, 4891-4932.
Elvidge, J.A.; Linstead, R.P.J. Chem. Soc. 1952, 5000-5007.
Mitsunori Nakamura et al.: "[pi]-Fused bis-BODIPY as a candidate for NIR dyes," Organic & Biomolcular Chemistry, vol. 10, No. 34, (Jan. 1, 2012), pp. 6840-6849.
English Abstract of Japanese Patent JP2002000275.
Yuu Kikukawa et al., "Facile one-pot preparation of thermally and photochemically convertible soluble precursors of copper phthalocyanine and naphthalocyanine", Chem. Commun., 2011, 47, 8518-8520.
Yu, Changjiang et al., "Highly Fluorescent BF2 Complexes of Hydrazine-Schiff Base Linked Bispyrrole", Org. Lett. 2014, 16, 3048-3051.
Stuart W. Oliver et al., "Oligomeric Cyclization of Dinitriles in the Synthesis of Phthalocyanines and Related Compounds: the Role of the Alkoxide Anion", J. Chem. Soc. Perkin Trans. 11 1987, 1579-1582.
Valentina F. Donyagine et al., "Synthesis of N,N-difluoroboryl complexes of 3,3'-diarylazadiisoindolylmethenes", Tetrahedron Letters 49 (2008) 6152-6154.

*Primary Examiner* — Michael Barker
(74) *Attorney, Agent, or Firm* — Renner Kenner Greive Bobak Taylor and Weber

(57) ABSTRACT

Half-phthalocyanine-like chelates, such as bis(iminoisoindolinyl)azomethene (BIAM), bis(oxoisoindolinyl)azomethene (BOAM), are provided, as well as chelates based thereon. Methods for synthesizing and synthetically modifying the novel chelate compounds are also provided. The half-phthalocyanine-like chelates have useful properties, particularly with regard to UV-visible absorption and emission as well as electron or energy transfer.

18 Claims, 10 Drawing Sheets

HALF-PHTHALOCYANINE-LIKE CHELATES AND SYNTHESIS THEREOF

RELATED APPLICATIONS

This application claims the benefit of U.S. Provisional Application No. 61/912,208, filed on Dec. 5, 2013, which is incorporated herein by reference.

TECHNICAL FIELD

The present invention relates to half-phthalocyanine-like chelates, and more specifically to the novel compounds bis (iminoisoindolinyl)azomethene (BIAM), bis(oxoisoindolinyl) azomethene (BOAM), and chelates based thereon. The present invention further relates to methods for synthesizing and synthetically modifying the chelate compounds, which have useful properties, particularly with regard to UV-visible absorption and emission as well as electron or energy transfer.

BACKGROUND OF THE INVENTION

Fluorescent chromophores have become essential to modern chemical investigations. Chromophores with high quantum yields of emission, such as fluorescein, coumarin and arylmethine dyes, have been used in applications ranging from biological imaging and sensing to light harvesting.

Pyrrole based chromophores have long played central roles in chemistry and related fields. Fluorescent chromophores have become essential to modern chemical investigations. Chromophores with high quantum yields of emission, such as fluorescein, coumarin and arylmethine dyes, have been used in applications ranging from biological imaging and sensing to light harvesting.

The archetypal polypyrrole is porphyrin, a tetrapyrrolic aromatic macrocycle that is common in biology (as an enzyme and protein cofactor) and has a rich synthetic chemistry. Porphyrin and its metal complexes have many applications as dyes, sensors, catalysts and components of advanced materials, such as photovoltaics. Pyrrole has also been used to generate alternate macrocycles (such as corrole, porphycene, or N-confused porphyrin), conjugated polymers, and chelates.

Dipyrromethenes are non-macrocyclic, pyrrole-based chelates. These compounds can be readily generated via the condensation of two equivalents of pyrrole and one equivalent of an aldehyde (although other synthetic methods have been employed), and the resultant conjugated chelates can be stabilized by coordination to a metal or main group ion.

Some of the more successful fluorophores in the literature belong to the boron-dipyrromethene (BODIPY®) family of compounds. Also known as 4,4-difluoro-4-bora-3a,4a-diaza-s-indacene, BODIPY is a small molecule that absorbs visible light near 500 nanometers (nm). These dyes, which are comprised of a dipyrromethene bound to a central $BF_2$ unit, have several optimal characteristics, including a large molar absorptivity, a high quantum yield of emission, and a reasonably sized Stokes shift. Quantum yield is close to unity in both organic solvents and water, allowing BODIPY to have a wide range of applications.

The BODIPY core can be functionalized at different peripheral positions to tune its fluorescence and expand its uses. For example, the BODIPY core can be attached to various biomolecules to enhance imaging in cells and in clinical diagnosis of disease. More recently, these compounds have been investigated as potential photosensitizers. In addition to biotechnology applications, BODIPY molecules are useful as dyes in material chemistry and optics, organic light-emitting diodes (OLED), and photovoltaic materials. The success of the BODIPY dyes and related compounds has spurred investigations into similar systems, such as the nitrogen substituted aza-BODIPY variants.

The meso carbon of the BODIPY core can be replaced by a nitrogen atom to form an aza-BODIPY. The latter does share some properties of the normal BODIPY. Both BODIPY and aza-BODIPY are highly fluorescent and have a high extinction coefficient. Both also absorb strongly in the UV region but aza-BODIPY absorbance is red-shifted (>500 nm). Both BODIPY and aza-BODPY require multiple steps for their synthesis, and the precursor to BODIPY, dipyrromethene, is an unstable molecule.

In spite of the extensive chemistry of isoindoline precursors to generate phthalocyanine macrocycles, the use of this chemistry to make a phthalocyanine analog of BODIPY is largely unexplored. Such a variant would require two changes to the BODIPY skeleton: the substitution of a nitrogen atom for the bridging carbon atom position, and the conversion of the pyrrole units to isoindoline rings. To date, there have been few examples of "half-phthalocyanine" like chelates. The synthesis methods that have been reported in the literature are non-trivial, and have limited versatility.

SUMMARY OF THE INVENTION

The present invention provides a compound represented by the structure:

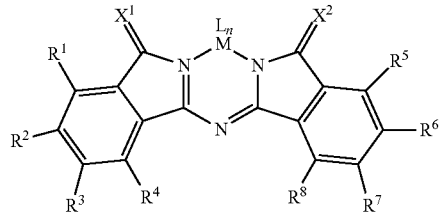

where M, L, n, each X and each R are described herein.

The present invention further provides a chromophoric chelate comprising a compound that is composed of two isoindoline moieties coordinated through the isoindolinyl nitrogen to a central atom, a bridging nitrogen atom that is covalently bonded to a carbon atom that is alpha to the isoindolinyl nitrogen in the 5-member ring of each isoindoline moiety, and a substituent that is doubly bonded to one or both of the alternate alpha carbons.

The present invention further provides a method for preparing a bis-isoindoline compound, the method comprising the step of reacting ingredients including a metal-based or main group-based Lewis acid and an isoindoline having at least one imino group in an alpha position, in the presence of a Bronsted-Lowry base, and optionally in the presence of a solvent.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
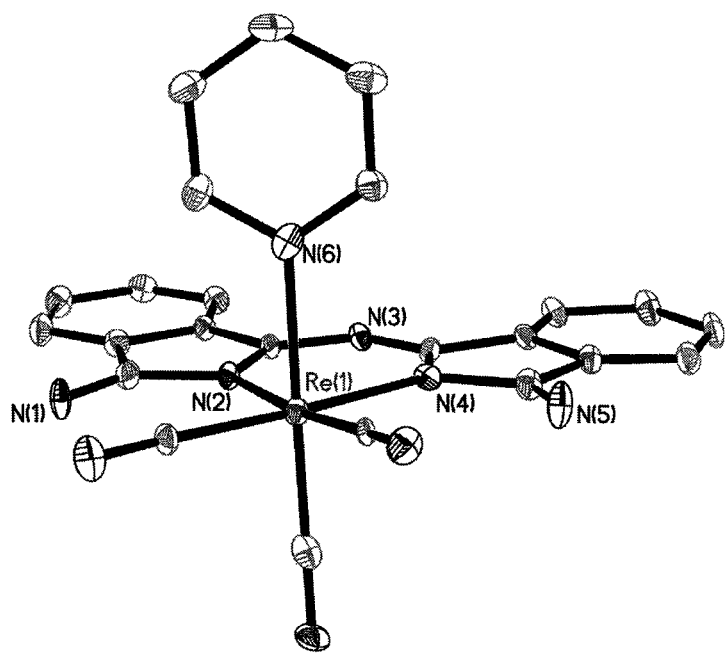
FIG. 1 is a representation of the molecular structure of $Re(CO)_3(BIAM)py$.

In general, the present invention provides novel half-phthalocyanine-like compounds that are composed of two isoindoline moieties coordinated through the isoindolinyl nitrogen to a central atom, and a bridging nitrogen atom that is covalently bonded to a carbon atom that is alpha to the isoindolinyl nitrogen in the 5-member ring of each isoindoline moiety. In one or more embodiments, the compounds of the present invention further include substituents that are doubly bonded to the alternate alpha carbons. Advantageously, the invention provides coupled isoindoline dimers rather than macrocycles.

In one or more embodiments, the present invention provides a new bis(iminoisoindolinyl)azomethene based compound, which may generally be referred to as BIAM, as well as the oxo version bis(oxoisoindolyl)azomethene, which may generally be refer to as BOAM. It should be understood that alternate terminology, such as di(iminoisoindolinyl) azomethene or di(iminoisoindolinyl)oxomethene) may also be employed, and in this case, the abbreviations may be DIAM and DOAM, respectively.

Complexes of BIAM are also provided. Indeed, many variations and derivatives of this novel core compound are envisioned, and a non-limiting sampling is described herein. Advantageously, in one or more embodiments, the BIAM compounds of the present invention are chromophoric and/or fluorescent, and may be referred to as chromophores, fluorophores, fluorophoric, fluorochromes, or the like. Many applications for this broad family of compounds are envisioned, and a non-limiting sampling of applications is described herein.

I. Novel Compounds

In one or more embodiments, the inventive compound comprises two isoindoline units, a bridging nitrogen atom that is bonded to an alpha carbon of each isoindoline unit, and two terminal moieties that are doubly bonded to the alternate alpha carbons via a nitrogen, oxygen, sulfur or carbon atom. In one or more embodiments, the compounds may be referred to as "half-phthalocyanines," or "bis(isoindolinyl) azomethenes" compounds. In one or more embodiments, the compounds may be represented by the structure

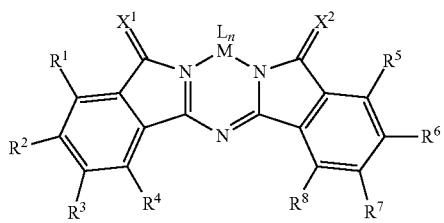

where M is an element that is capable of templating the formation of a chelate, each L is independently selected from moieties that are capable of forming a ligand with M, and where n is an integer from 0 to 4. In one or more embodiments, n is an integer from 2 to 4. In one or more embodiments, M is an element that is kinetically inert. In one or more embodiments, M is an element that is capable of forming a chelate rather than a phthalocyanine macrocycle. In one or more embodiments, M is boron, gallium, phosphorus, rhenium, ruthenium, cobalt, or chromium.

The R groups in the above structure are not particularly limited. It will be understood that substituents may be selected to provide appropriate properties and/or reactivity.

In one or more embodiments, each R is independently selected from chemical moieties that will form a covalent bond with one or more of the cyclic carbon atoms in the above structure. Furthermore, it is envisioned that two or more R groups may combine to form cyclic or heterocyclic moieties.

In one or more embodiments, the half-phthalocyanine-like compound is unsubstituted, or in other words, $R^1$, $R^2$, $R^3$, $R^4$, $R^5$, $R^6$, $R^7$, and $R^8$ are hydrogen.

In one or more embodiments, each R is independently selected from hydrogen, hydroxyl, branched or unbranched, saturated or unsaturated monovalent organic groups, nitrogen-containing moieties, halogen, halogenated moieties, oxygen-containing moieties, phosphorus-containing moieties, silicon-containing moieties, and sulfur-containing moieties, or two or more R groups may together to form an optionally substituted cyclic or heterocyclic moiety. The optionally substituted cyclic or heterocyclic moiety may be monocyclic or multicyclic.

In one or more embodiments, monovalent organic groups include hydrocarbyl groups. In one or more embodiments, each hydrocarbyl group may contain from 1 to about 30 carbon atoms. In one or more embodiments, these groups may include from about 2 to about 25 carbon atoms, in other embodiments, from about 3 to about 20 carbon atoms, in other embodiments, from about 4 to about 10 carbon atoms, and in other embodiments, 8 or less carbon atoms. These hydrocarbyl groups can include, but are not limited to, alkyl, cycloalkyl, substituted alkyl, substituted cycloalkyl, alkenyl, cycloalkenyl, substituted alkenyl, substituted cycloalkenyl, aryl, substituted aryl, allyl, aralkyl, alkaryl, and alkynyl groups, and may contain hetero atoms such as N, O, S, P, and Si. In one or more embodiments, where these hydrocarbyl groups include O, they may be referred to as oxo-hydrocarbyl groups, where the include S, they may be referred to as sulfo-hydrocarbyl groups, or where they include N, they may be referred to as aza-hydrocarbyl groups.

Specific examples of hydrocarbyl groups include methyl, ethyl, propyl, isopropyl, butyl, 2-methylbutyl, pentyl, hexyl, cyclohexyl, heptyl, octyl, cyclo-octyl, 2-ethylhexyl, and 2-propylhexyl. Examples of nitrogen-containing moieties include amine, amide, imine, imide, azide, azo, cyanates, nitrates, nitriles, nitrite, nitro, nitroso, pyridine. Examples of sulfur-containing moieties include thiols, and thiocyanates.

In one or more embodiments, $X^1$ and $X^2$ are independently selected from oxygen, sulfur, imine groups and alkenyl groups. In one or more embodiments, $X^1$ and $X^2$ are independently selected from oxygen, sulfur, $NR^a$, and $C(R^b)_2$ In one or more embodiments, $R^a$ and each $R^b$ are independently selected from hydrogen, an alkyl group, and an aryl group.

In one or more embodiments, substituents $R^1$, $R^2$, $R^3$, $R^4$, $R^5$, $R^6$, $R^7$, and $R^8$ are independently selected from hydrogen, hydroxyl, halogen, alkyl, carboxyalkyl, aryl, sulfo, isocyanate, isothiocyanate, and formyl, alone or in combination. Suitable substituents include any substituent that is described for BODIPY in U.S. Pat. No. 4,774,339, or for BOPHY in co-pending International Patent Application Serial No. PCT/US2014/66568, filed on Nov. 20, 2014, both of which are hereby incorporated by reference.

In one or more embodiments, any adjacent R and R groups, taken together with any intervening atoms, comprise a group chosen from an optionally substituted monocyclic group and an optionally substituted $C_{6-24}$ multicyclic group.

In one or more embodiments, $R^1$ is selected from hydrogen, an alkyl group, and a cyano group, or $R^2$ and $R^1$ taken together with any intervening atoms comprise a group chosen from an optionally substituted monocyclic group and an optionally substituted $C_{6-24}$ multicyclic group.

In one or more embodiments, $R^2$ is selected from hydrogen, an alkyl group, and a cyano group, or $R^1$ and $R^2$ taken together with any intervening atoms comprise a group chosen from an optionally substituted monocyclic group and an optionally substituted $C_{6-24}$ multicyclic group, or $R^2$ and $R^3$ taken together with any intervening atoms comprise a group chosen from an optionally substituted monocyclic group and an optionally substituted $C_{6-24}$ multicyclic group. In one or more embodiments, the optionally substituted monocyclic and multicyclic groups are chosen from aryl and heteroaryl groups.

In one or more embodiments, $R^3$ is selected from hydrogen, an alkyl group, and a cyano group, or $R^2$ and $R^3$ taken together with any intervening atoms comprise a group chosen from an optionally substituted monocyclic group and an optionally substituted $C_{6-24}$ multicyclic group, or $R^4$ and $R^3$ taken together with any intervening atoms comprise a group chosen from an optionally substituted monocyclic group and an optionally substituted $C_{6-24}$ multicyclic group. In one or more embodiments, the optionally substituted monocyclic and multicyclic groups are chosen from aryl and heteroaryl groups.

In one or more embodiments, $R^4$ is selected from hydrogen, an alkyl group, and a cyano group, or $R^4$ and $R^3$ taken together with any intervening atoms comprise a group chosen from an optionally substituted monocyclic group and an optionally substituted $C_{6-24}$ multicyclic group.

In one or more embodiments, $R^5$ is selected from hydrogen, an alkyl group, and a cyano group, or $R^5$ and $R^6$ taken together with any intervening atoms comprise a group chosen from an optionally substituted monocyclic group and an optionally substituted $C_{6-24}$ multicyclic group.

$R^6$ is chosen from hydrogen, an alkyl group, and a cyano group, or $R^6$ and $R^7$ taken together with any intervening atoms comprise a group chosen from an optionally substituted monocyclic group and an optionally substituted $C_{6-24}$ multicyclic group, or $R^6$ and $R^5$ taken together with any intervening atoms comprise a group chosen from an optionally substituted monocyclic group and an optionally substituted $C_{6-24}$ multicyclic group.

$R^7$ is chosen from hydrogen, an alkyl group, and a cyano group, or $R^8$ and $R^7$ taken together with any intervening atoms comprise a group chosen from an optionally substituted monocyclic group and an optionally substituted $C_{6-24}$ multicyclic group, or $R^7$ and $R^6$ taken together with any intervening atoms comprise a group chosen from an optionally substituted monocyclic group and an optionally substituted $C_{6-24}$ multicyclic group.

$R^8$ is chosen from hydrogen, an alkyl group, and a cyano group, or $R^8$ and $R^9$ taken together with any intervening atoms comprise a group chosen from an optionally substituted monocyclic group and an optionally substituted $C_{6-24}$ multicyclic group.

In one or more embodiments, $R^1$, $R^2$, $R^3$, $R^4$, $R^5$, $R^7$, and $R^8$ are independently selected from of $C_1$-$C_{30}$ alkyl, $C_1$-$C_{30}$ alkenyl, $C_1$-$C_{30}$ alkynyl, $C_1$-$C_{30}$ aryl, $C_1$-$C_{30}$ alkoxy, $C_1$-$C_{30}$ phenoxy, $C_1$-$C_{30}$ thioalkyl, $C_1$-$C_{30}$ thioaryl, $C_1$-$C_{30}$C(O)OR$^{11}$, N(R$^{12}$)(R$^{13}$), C(O)N(R$^{11}$)(R$^{12}$), F, Cl, Br, NO$_2$, CN, acyl, carboxylate, and hydroxyl, wherein $R^{11}$, $R^{12}$ and $R^{13}$ are independently selected from the group of hydrogen, $C_1$-$C_{30}$ alkyl, and $C_1$-$C_{30}$ aryl.

In one or more embodiments, $R^1$ and $R^5$ may be the same. In one or more embodiments, $R^2$ and $R^7$ are the same. In one or more embodiments, $R^2$ and $R^6$ are the same. In one or more embodiments, $R^3$ and $R^7$ are the same. In one or more embodiments, $R^4$ and $R^8$ are the same. Thus, in one or more embodiments, the compounds may be referred to as dimers.

II. Synthesis

Advantageously, the novel bis-iminoisoindoline compounds may be prepared via a one-step reaction involving template synthesis. In one or more embodiments, Lewis acids can be used as templates to generate chelate-like structures. By restricting the formation of a chelate around the equatorial positions of the template, a coupled isoindoline dimer rather than a macrocycle may be formed, as generally shown in Scheme 1.

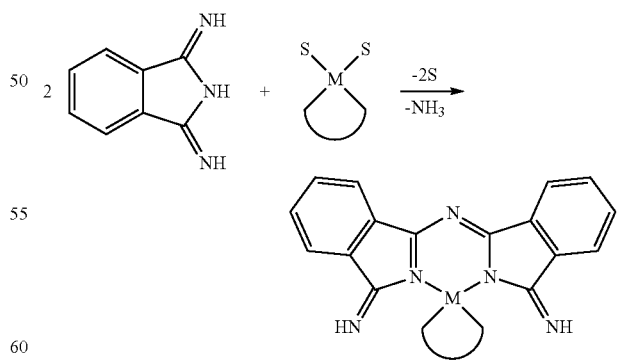

In Scheme 1 shown above, the M-half circle diagram represents a Lewis acidic molecule, composed of either a metal ion complex or a main group compound, having two labile groups (represented by "S"). Removal of one or both of the "S" groups allows for isoindoline coordination. The circle represents non-labile moieties that remain bound to M and prevent formation of a macrocyle. Suitable non-labile moieties include monodentate ligands and chelating groups.

While Scheme 1 shows the use of a diiminoisoindoline starting material, and suggests that two equivalents of a single starting material are employed, the invention is not to be so limited. In one or more embodiments, two or more distinct isoindoline reagents may be employed. Also, it is not necessary that the isoindoline reagent contain two imino groups, so long as the isoindoline reagent contains at least one imino group in an alpha position.

Thus, the present invention further provides a method for preparing a bis-iminoisoindoline compound, the method comprising the step of reacting a metal-based or main group-based Lewis acid with an isoindoline having at least one imino group in an alpha position, under conditions conducive to a condensation reaction.

More specifically, in one or more embodiments, a bis-isoindoline compound may be prepared by combining a Lewis acid and a substituted or unsubstituted iminoisoindoline in the presence of a Bronsted-Lowry base, and optionally in the presence of a solvent.

In one or more embodiments, the method comprises the step of reacting a metal-based or main group-based Lewis acid with a substituted or unsubstituted 1,3-diiminoisoindoline (DII). In one or more embodiments, a bis-isoindoline compound may be prepared by combining a Lewis acid and 2 equivalents of a substituted or unsubstituted 1,3-diiminoisoindoline in the presence of a Lewis base, and optionally in the presence of a solvent. The solvent is not particularly limited, but may be selected based upon solubility of the reactants and products. Examples of solvents include chlorobenzene.

In one or more embodiments, a coordinating ligand compound may be included, such as pyridine or N-methyl imidazole, to form a bidentate chelate, rather than a tridentate or higher denticity chelate. In one or more embodiments, one S may remain bound to the M.

In one or more embodiments, the synthesis may be represented by Scheme 2A below.

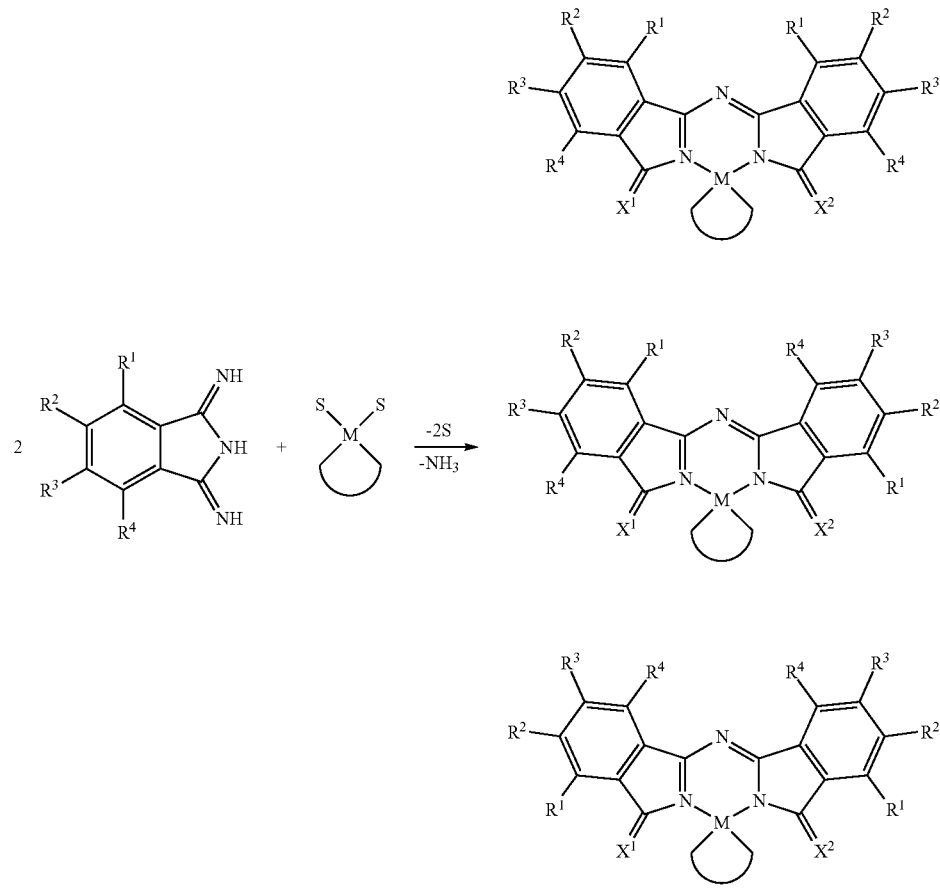

where M, each S, and each R are as defined above. In one or more embodiments, M is selected from the group consisting of boron, rhenium, gallium, phosphorus, ruthenium, cobalt, and chromium. In one or more embodiments, M is selected from the group consisting of boron and rhenium.

Non-limiting examples of suitable Lewis acids include boron, rhenium, gallium and phosphorous-based Lewis acids. More specific examples include boron trifluoride, phenyl boronic acid, pentacarbonylchlororhenium, triphenylboron, and the like.

In one or more embodiments, two or more distinct starting materials are reacted with a Lewis base to form the bis-isoindoline. Thus, a more general reaction scheme is represented in Scheme 1B below, where $R^6$, $R^7$, $R^8$, $R^9$, and $R^{10}$ may or may not be the same as or similar to $R^1$, $R^2$, $R^3$, $R^4$, and $R^5$, respectively.

Scheme 2B

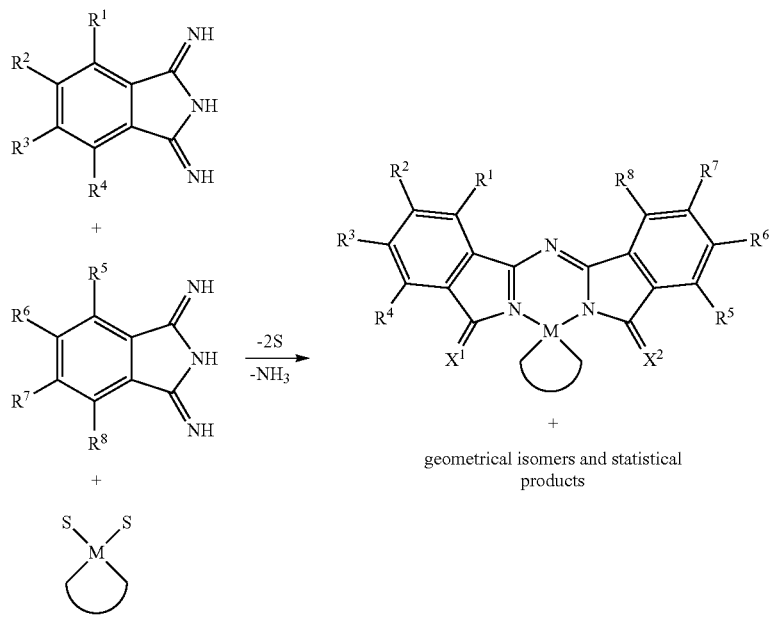

+ geometrical isomers and statistical products where each S, M, X, R and a are as described above. It will be understood that various geometrical isomers may be prepared in this manner, and isolated according to conventional methods.

In one or more embodiments, the isoindoline starting material(s) may be represented by the following structure:

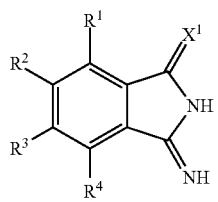

In one or more embodiments, $X^1$ and each R is independently as described above, with the proviso that the substituent does not interfere with the formation of the BIAM or BOAM structure. It is envisioned that two or more R groups may combine to form cyclic or heterocyclic moieties, with the proviso that the cyclic or heterocyclic substituent does not interfere with the formation of the BIAM or BOAM structure.

In one or more embodiments, the reaction occurs in the substantial absence of water. By substantial absence of water is meant that no more than trace quantities of water are present in the starting materials and the reaction environment. In one or more embodiments, the starting materials that are used in the reaction are denatured, or dried before use, no water is added to the reaction, and the reaction is conducted under dry atmospheric conditions.

Examples of suitable diiminoisoindolines include substituted or unsubstituted 1,3-diiminoisoindoline.

In one or more embodiments, the resultant BIAM compound may be readily purified via known methods.

In one or more embodiments, the BIAM compound may be hydrolyzed to produce a BOAM compound, or may be partially hydrolyzed to produce a compound containing both oxo- and iminoisoindoline moieties.

In one or more embodiments, the reaction exemplified in Schemes 2A or 2B above may be conducted under wet conditions. That is, water may be added, or may be present in the solvent or reactants. Under wet conditions, oxo- and/or imino-oxo isoindoline compounds may be formed, either alone or in combination with iminoisoindoline compounds.

III. Elucidation of Structure

Figure 2:
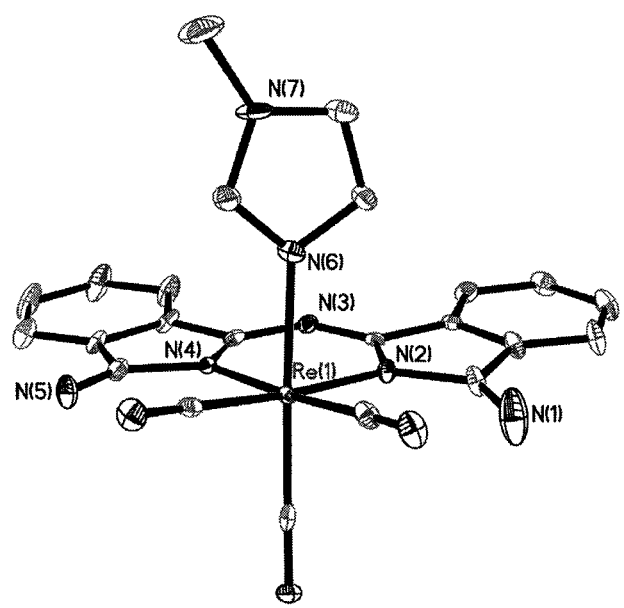
FIG. 2 is a representation of the molecular structure of $Re(CO)_3(BIAM)N\text{-MeIm}$.
Figure 3:
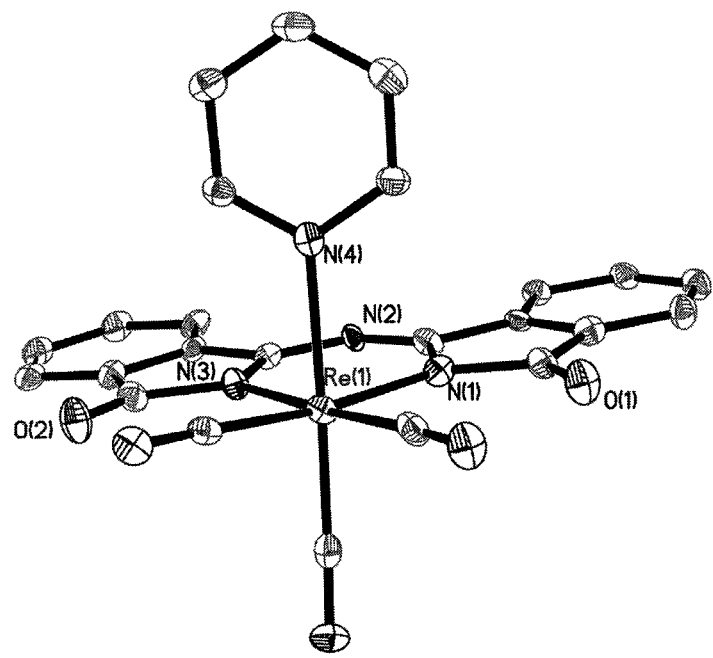
FIG. 3 is a representation of the molecular structure of Re(CO)₃(BOAM)py.
Figure 4:
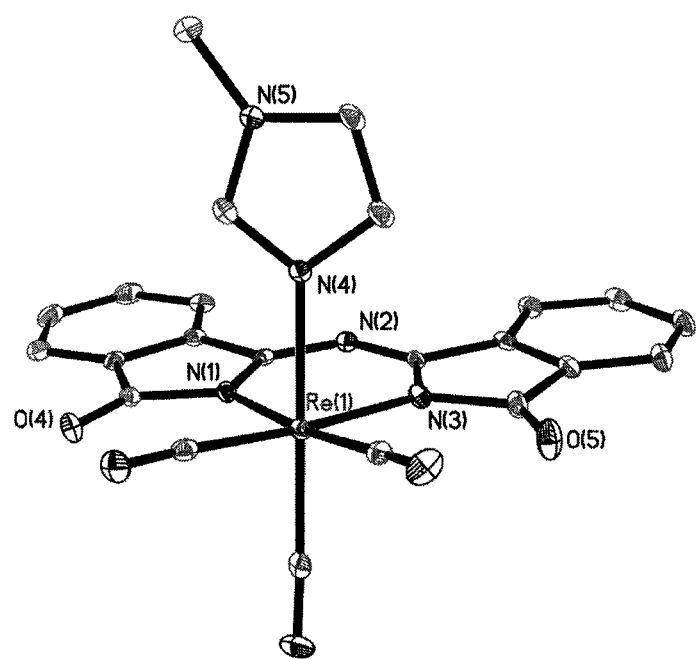
FIG. 4 is a representation of the molecular structure of Re(CO)₃(BOAM)N-MeIm.
Figure 5:
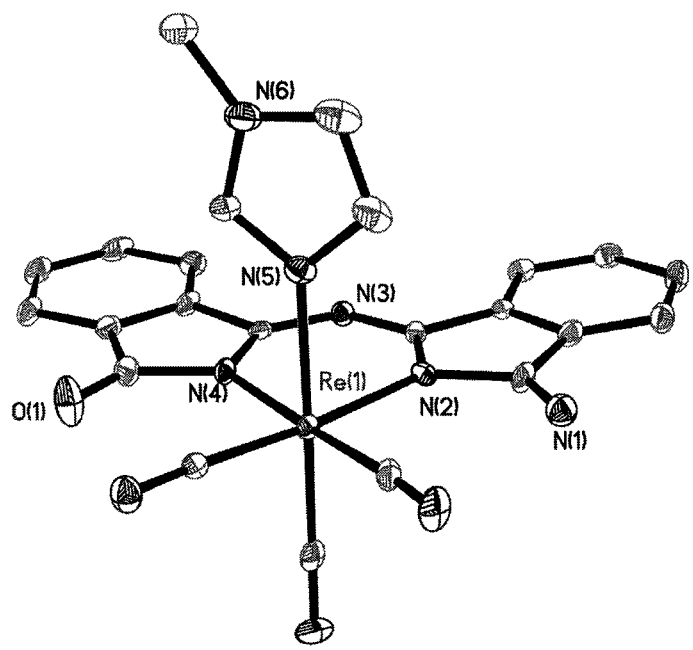
FIG. 5 is a representation of the molecular structure of Re(CO)₃(BIOAM)N-MeIm.
Figure 8:
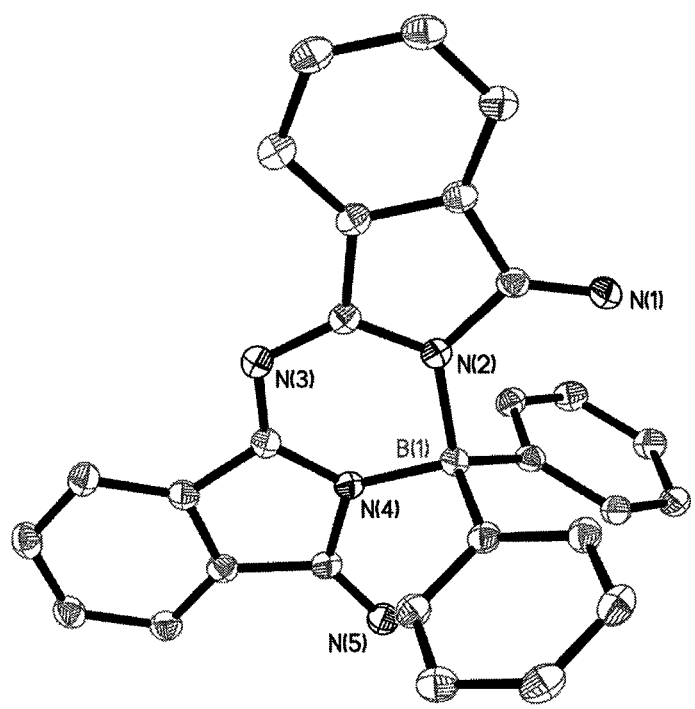
FIG. 8 is a representation of the molecular structure of BPh₂(BIAM).

The structures of BOAM and BIAM complexes may be elucidated via single crystal X-ray diffraction. Referring to the Figures, FIG. 1 is a representation of the molecular structure of $Re(CO)_3(BIAM)$, where L is pyridine (py). FIG. 2 is a representation of the molecular structure of $Re(CO)_3$ (BIAM), where L is N-methyl imidazole (N-MeIm). FIG. 3 is a representation of the molecular structure of $Re(CO)_3$ (BOAM), where L is py. FIG. 4 is a representation of the molecular structure of $Re(CO)_3(BOAM)$, where L is N-MeIm. FIG. 5 is a representation of the molecular structure of $Re(CO)_3(BIOAM)$, where L is N-MeIm. FIG. 8 is a representation of the molecular structure of bis(iminoisoindolinyl)azomethene diphenyl boron ($Ph_2B(BIAM)$).

IV. Properties

The BIAM or BOAM chromophoric core may be modified to include a wide variety of substituents. The core can be readily substituted at the isoindoline carbon positions. It will be understood that the substituents may affect properties such as absorption and emission. The nature of the modification allows the electronic properties to be carefully tuned. In one or more embodiments, the compounds of the present invention exhibit a bathochromic shift in their absorbance spectra. Such red shifts can be highly desirable in dye compounds.

Advantageously, the BIAM and BOAM cores are analogous to the BODIPY core, in that they may be functionalized at different peripheral positions to tune their fluorescence properties and expand their uses. Advantageously, unlike aza-BODIPY, the BOAM and BIAM family of compounds, including Ph$_2$B(BIAM), have high reactivity at the terminal X atom position where X is nitrogen, allowing for a wider range of products to be made.

The architectures of the BIAM and BOAM cores represent a new structural motif for highly fluorescent compounds. Additionally, the BIAM and BOAM structural motifs are an attractive target for functionalization at a variety of positions on the periphery.

V. Functionalization and Conjugation

In one or more embodiments, the BIAM and BOAM compounds described above, which may be referred to as the BIAM and BOAM cores, respectively, may be functionalized and/or conjugated by further reaction. Advantageously, the BIAM and BOAM cores may be functionalized and/or conjugated similarly to the BODIPY compounds. Reactions with BODIPY compounds are further described in Loudet et al., "BODIPY Dyes and Their Derivatives: Syntheses and Spectroscopic Properties," Chem. Rev. 2007, 107, 4891-4932; Yu, Changjiang et al., "Highly Fluorescent BF$_2$ Complexes of Hydrazine-Schiff Base Linked Bispyrrole," Org. Lett. 2014, 16, 3048-3051; U.S. Pat. No. 5,189,029, International Patent No. WO 9419355; U.S. Pat. No. 5,498,641; U.S. Pat. No. 5,189,029; U.S. Pat. No. 361,936; Japanese Patent No. 11176572; Japanese Patent No. 10273504; Japanese Patent No. 2000001509; Japanese Patent No. 2000001510; Japanese Patent No. 2000039715; Japanese Patent No. 2000039716; U.S. Pat. No. 4,774,339; U.S. Pat. No. 5,433,896; and U.S. Pat. No. 6,005,113, all of which are hereby incorporated by reference. In one or more embodiments, mono-substituted compounds may be achieved. In one or more embodiments, di-substituted products may be achieved. In one or more embodiments, the BIAM and BOAM cores may be substituted at more than two sites. For example, in one or more embodiments, tetra-substituted products may be achieved.

VI. Uses—

In general, the BIAM and BOAM families of compounds may be used in many, if not all, of the applications in which BODIPY compounds have been employed. The BIAM and BOAM cores may be used to generate fluorescent conjugates of peptides, proteins, nucleotides, oligonucleotides and dextrans. The BIAM and BOAM cores may be used to prepare derivatives and conjugates that are useful as fluorescent enzyme substrates, fatty acids, phospholipids, lipopolysaccharides, receptor ligands and polystyrene microspheres.

In addition, BIAM and BOAM compounds, derivatives and conjugates thereof, may be used in polymers, photovoltaics, circuitry, and other material science applications.

The compounds of the present invention and/or their derivatives and conjugates find potential utility as alternatives to BODIPY compounds in applications described in U.S. Pat. Nos. 5,728,529, 5,804,395, 5,861,287, 5,994,063, 6,340,750, 8,426,850, International Patent Appl. Pub. Nos. WO 03/066812 A2, WO 2010/051530 A2, all of which are hereby incorporated by reference.

In order to demonstrate the practice of the present invention, the following examples have been prepared and tested. The examples should not, however, be viewed as limiting the scope of the invention. The claims will serve to define the invention.

EXAMPLES

GENERAL INFORMATION: All reagents were purchased from TCI Chemical, Acros Organics or Sigma-Aldrich and used as received.

Synthesis—

1,3-Diiminoisoindoline (DII) was prepared according to the modified procedure described in Elvidge, J. A.; Linstead, R. P. *J. Chem. Soc.* 1952, 5000-5007, which is hereby incorporated by reference.

Figure 6:
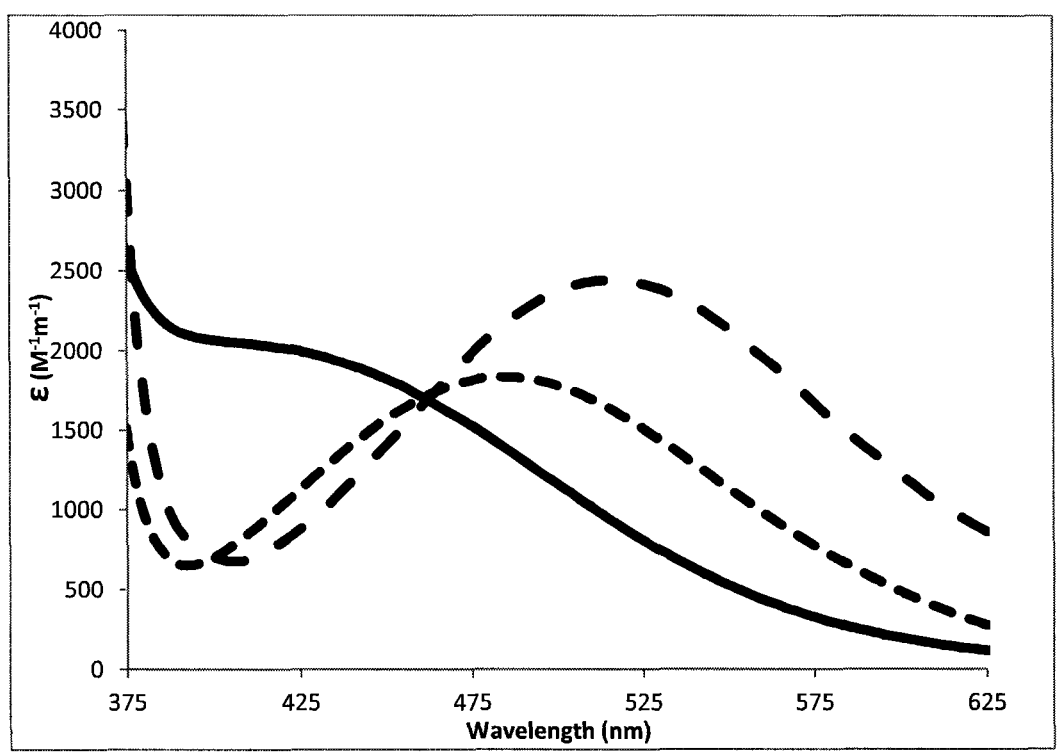
FIG. 6 is the UV-visible spectra in dichloromethane of Re(CO)₃(BIAM)py (solid line), Re(CO)₃(BIOAM)py (small dashed line), and Re(CO)₃(BOAM)py (large dashed line).

A rhenium complex (Re(CO)$_3$(BIAM)py) was prepared as follows:

40.4 milligrams (mg) (0.112 millimoles (mmol)) of Re(CO)$_5$Cl and 32.2 mg (0.229 mmol) of DII were refluxed in dry chlorobenzene for 3 hours. 0.11 milliliters (mL) of 1 M pyridine in chlorobenzene was then added and refluxed overnight. The orange solid was collected and washed with diethyl ether and dried overnight. Crystals were grown by slow evaporation of dimethylformamide. Yield: 15.9 mg, 22.8%. Infrared spectrum (v, cm$^{-1}$): CO 2008, 1889, NH 3439. Elemental analysis: C$_{24}$H$_{15}$N$_6$O$_3$Re•1.8C$_3$H$_7$NO•1.6CH$_2$Cl$_2$ found C, 41.15%; H, 2.78; N, 12.99. calculated C, 41.88%; H, 3.49%; N, 12.29%. $^1$H NMR (300 MHz, DMSO) δ=10.51 (s11H), 8.18 (d, J=8.49 Hz, 1H), 8.10 (d, 8.20 HZ, 1H), 7.69 (m, 8H), 7.36 (t, J=7.61 Hz, 1H), 8=6.98 (d, J=7.32 Hz, 1H). MALDI (positive ion) [M+H]$^+$-pyridine calcd m/z=544.0419. found m/z=544.0413. The molecular structure is shown in FIG. 1. The UV-visible absorbance spectrum in dichloromethane is shown in FIG. 6.

Figure 7:
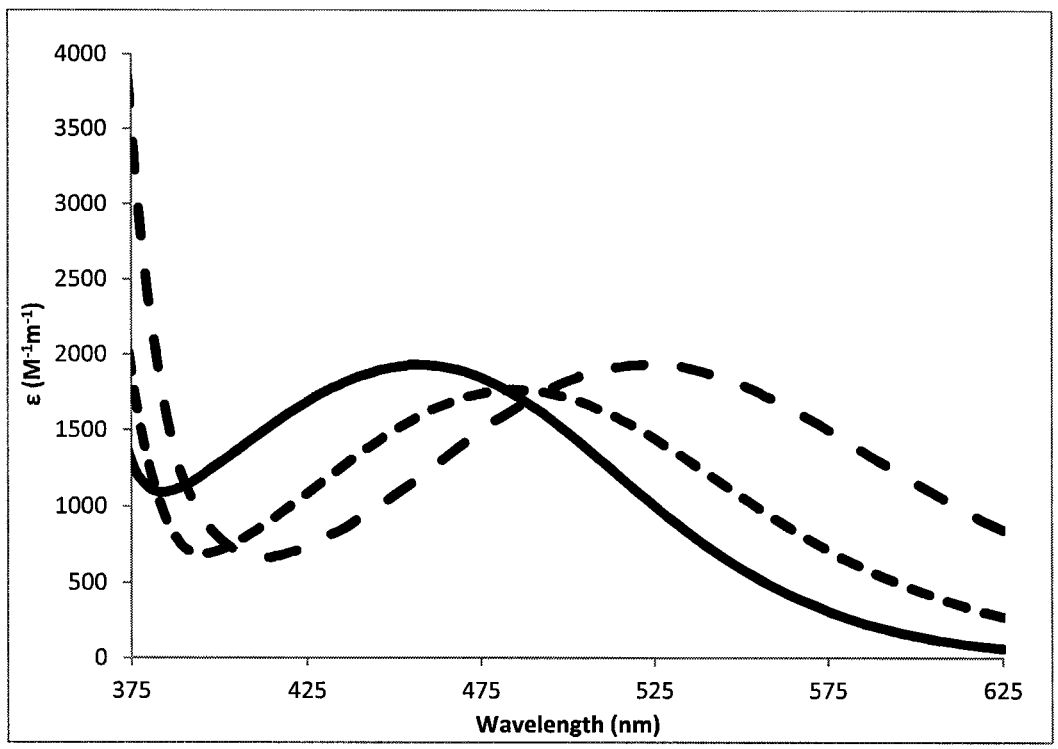
FIG. 7 is the UV-visible spectra in dichloromethane of Re(CO)₃(BIAM)N-MeIm (solid line), Re(CO)₃(BIOAM)N-MeIm (small dashed line), and Re(CO)₃(BOAM)N-MeIm (large dashed line).

Re(CO)$_3$(BIAM)N-MeIm was prepared as follows:

40.9 mg (0.113 mmol) of Re(CO)$_5$Cl and 32.0 mg (0.221 mmol) of 1 were refluxed in dry chlorobenzene for 3 hours. 0.11 mL of 1 M N-methyl imidazole in chlorobenzene was then added and the reaction refluxed overnight. The orange solid was collected and washed with diethyl ether then dried overnight. Crystals were grown by the slow evaporation of dimethylformamide. Yield: 16.9 mg, 24.5%. Infrared spectrum (v, cm$^{-1}$): CO 2004, 1896, NH 3439. Elemental analysis C$_{23}$H$_{16}$N$_7$O$_3$Re•0.1C$_4$H$_7$N$_2$•2.05H$_2$O.•0.8C$_5$H$_5$Cl found C, 43.99%; H, 3.50%; N, 13.29%. calculated C, 43.86%; H, 3.33%; N, 13.44%. $^1$H NMR (300 MHz, CDCl$_3$) δ=8.30 (s, 1H), 8.11 (s, 1H), 8.01 (d, J=7.0 Hz 1H), 7.69 (m, 6H), 7.20 (t, J=1.46 Hz 1H), 7.05 (t, J=1.8 Hz, 1H). ESI (positive ion) [M+H]$^+$-N-methyl imidazole calcd m/z=544.0419. found m/z=544.0485. The molecular structure is shown in FIG. 2. The UV-visible absorbance spectrum in dichloromethane is shown in FIG. 7.

Structures of these two compounds are comprised of the expected facial geometry of the Re(CO)$_3$ unit, a bidentate BIAM ligand, and a sixth monodentate ligand site occupied by either pyridine or N-methylimidazole. The BIAM ligand is monoanionic, which is indicative of the electronic delocalization across the ligand molecule.

Figure 10:
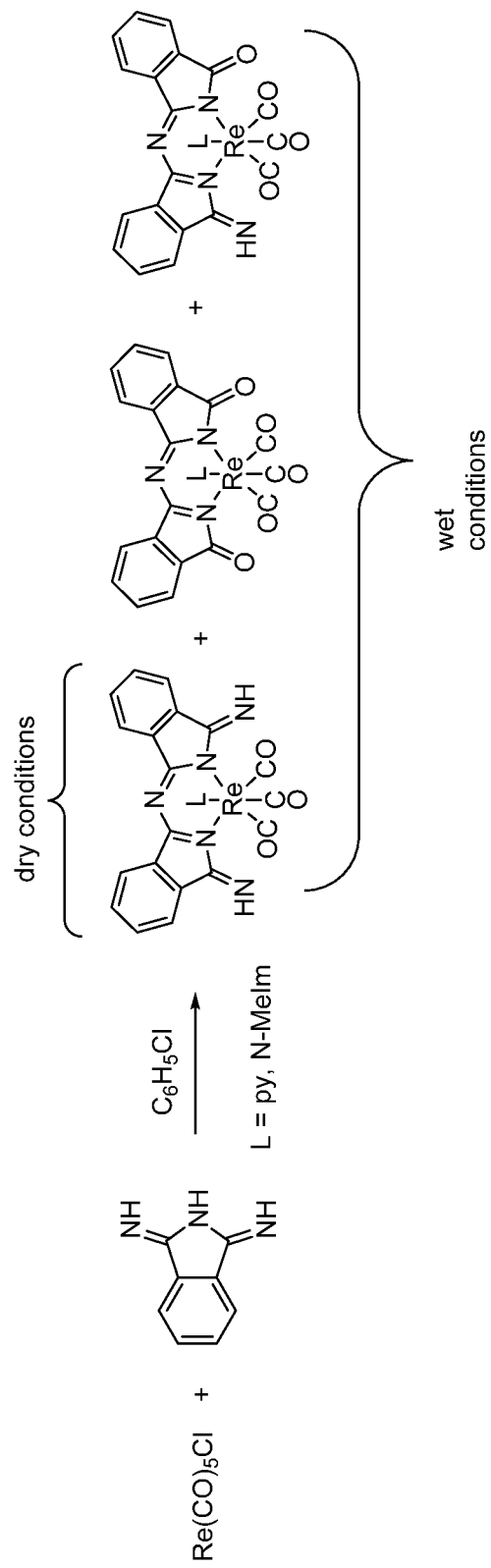
FIG. 10 schematically portrays the use of Re(CO)₃ as a template for BIAM, BOAM and mixed chelates (top), and the structures of several examples of isoindoline-chelate Re(CO)₃ compounds (bottom).

In one or more embodiments, when the same reaction is carried out under wet conditions (either with undried solvent or in the presence of excess water), both partial and complete hydrolysis of the terminal imine bonds, is observed, as also shown in FIG. 10. Simple chromatographic methods can be used to separate these compounds, which upon structural elucidation revealed a mixture of the bis-imino, bis-oxo and mixed imino-oxo compounds.

Re(CO)$_3$(BOAM)py was prepared as follows:

40.4 mg (0.112 mmol) of Re(CO)$_5$Cl and 31.6 mg (0.218 mmol) of DII were refluxed in wet chlorobenzene for 3 hours. 0.11 mL of 1 M pyridine in chlorobenzene was then added and the reaction refluxed overnight. The reaction was rotary evaporated to dryness. The Re(CO)$_3$(BOAM)py product was purified as the first fraction via chromatography on silica gel using dichloromethane as the eluent. Yield: 13.9 mg, 19.9%. Infrared spectrum (v, cm$^{-1}$): v CO 2007, 1871. Elemental analysis C$_{24}$H$_{13}$N$_4$O$_5$Re•0.9H$_2$O•1.15CH$_2$Cl$_2$, C, 40.77%;

H, 2.12%; N, 7.81%; calculated C, 40.96%; H, 2.34%; N, 7.60%. $^1$H NMR (300 MHz, CDCl$_3$) δ=8.72 (d, J=6.6 Hz, 1H), 8.52 (d, J=6.6 Hz, 1H), 7.95 (m, 2H), 7.79 (m, 2H) 7.61 (m, 4H), 7.28 (t, J=6.4 Hz, 2H), δ=7.15 (t, J=6.4 Hz, 1H). ESI (positive ion) [M+H]$^+$ calcd m/z=625.0522. found m/z=625.0599. The molecular structure is shown in FIG. 3. The UV-visible absorbance spectrum in dichloromethane is shown in FIG. 6.

Re(CO)$_3$(BOAM)N-MeIm was prepared as follows:

40.2 mg (0.111 mmol) of Re(CO)$_5$Cl and 34.6 mg (0.239 mmol) of DII were refluxed in wet chlorobenzene for 3 hours. 0.11 mL of 1 M N-methyl imidazole in chlorobenzene was then added and the reaction refluxed overnight. The reaction was rotary evaporated to dryness. The Re(CO)$_3$(BOAM)N-MeIm product was purified as the first fraction via chromatography on silica gel using dichloromethane as the eluent. Yield: 19.2 mg, 27.5%. Infrared spectrum (v, cm$^{-1}$): v CO 2010, 1878. Elemental analysis C$_{23}$H$_{14}$N$_5$O$_5$Re•1.4H$_2$O•0.2C$_4$H$_7$N$_2$ found, C, 42.54%; H, 2.43%; N, 11.33%. calculated C, 42.82%; H, 2.73%; N, 11.33%. $^1$HNMR (300 MHz) δ=8.00 (m, 2H), δ=7.81 (m, 2H), δ=7.63 (m, 4H), δ=7.56 (s, 1H), δ=6.91 (t, 1.0 Hz, 1H), δ=6.64 (t, 1.6 Hz, 1H), δ=3.57 (s, 3H). MALDI-MS (positive ion) [M+H]$^+$-methylimidazole calcd m/z=546.010. found m/z=545.951. The molecular structure is shown in FIG. 4. The UV-visible absorbance spectrum in dichloromethane is shown in FIG. 7.

Re(CO)$_3$(BIOAM)py was prepared as follows:

The same procedure was used as Re(CO)$_3$(BOAM)py. The Re(CO)$_3$(BIOAM)py was collected as the second fraction via chromatography on silica gel using dichloromethane as the eluent. Yield: 7.1 mg, 4.89%. Infrared spectrum (v, cm$^{-1}$): (CO) 2011, 1874. $^1$H NMR (300 MHz, CDCl$_3$) δ=11.68 (s, 1H), 8.66 (d, J=6.0 Hz, 2H), 8.49 (d, J=6.0 k Hz, 1H), 8.19-7.70 (m, 7H), 7.57 (t, J=6.4 Hz, 2H), 7.44 (t, J=6.4 Hz, 1H). ESI (positive ion) [M+H]$^+$ calcd m/z=623.0603. found m/z=623.9698. The molecular structure is shown in FIG. 5. The UV-visible absorbance spectrum in dichloromethane is shown in FIG. 6.

Re(CO)$_3$(BIOAM)N-MeIm was prepared as follows:

The same procedure was used as Re(CO)$_3$(BOAM)N-MeIm. The Re(CO)$_3$(BIOAM)N-MeIm was collected as the second fraction via chromatography on silica gel using dichloromethane as the eluent. Yield: 5.6 mg, 7.9% Infrared spectrum (v, cm$^{-1}$): (CO) 2007, 1892. $^1$H NMR (500 MHz, DMSO) δ=11.51 (s, 1H), 8.13 (d, J=6.60 Hz, 1H), 8.00 (m, 2H), 7.75 (m, 6H), 7.06 (s, 1H), 6.77 (s, 1H), 3.54 (s, 3H). ESI (positive ion) [M+H]$^+$ calcd m/z=627.0791. found m/z=626.0685. The molecular structure is shown in FIG. 4. The UV-visible absorbance spectrum in dichloromethane is shown in FIG. 7.

BPh$_2$(BIAM) was prepared as follows:

Triphenylboron, Ph$_3$B (0.097 g, 0.401 mmol) and DII (0.111 g, 0.766 mmol) were refluxed in dry chlorobenzene for 12 hours with the solution turning from clear to yellow-green. The reaction was rotary evaporated to dryness and purified via column chromatography on silica using CH$_2$Cl$_2$ as the eluting solvent. Yield: 77 mg, 23%. $^1$H NMR (300 MHz, CDCl$_3$) δ=9.07 (s, 2H), 8.15 (m, 4H), 7.96 (m, 4H), 7.72 (t, J=3.2, 4H), 7.54 (d, J=6.4 Hz, 2H), δ=7.31 (m, 6H).

Figure 9:
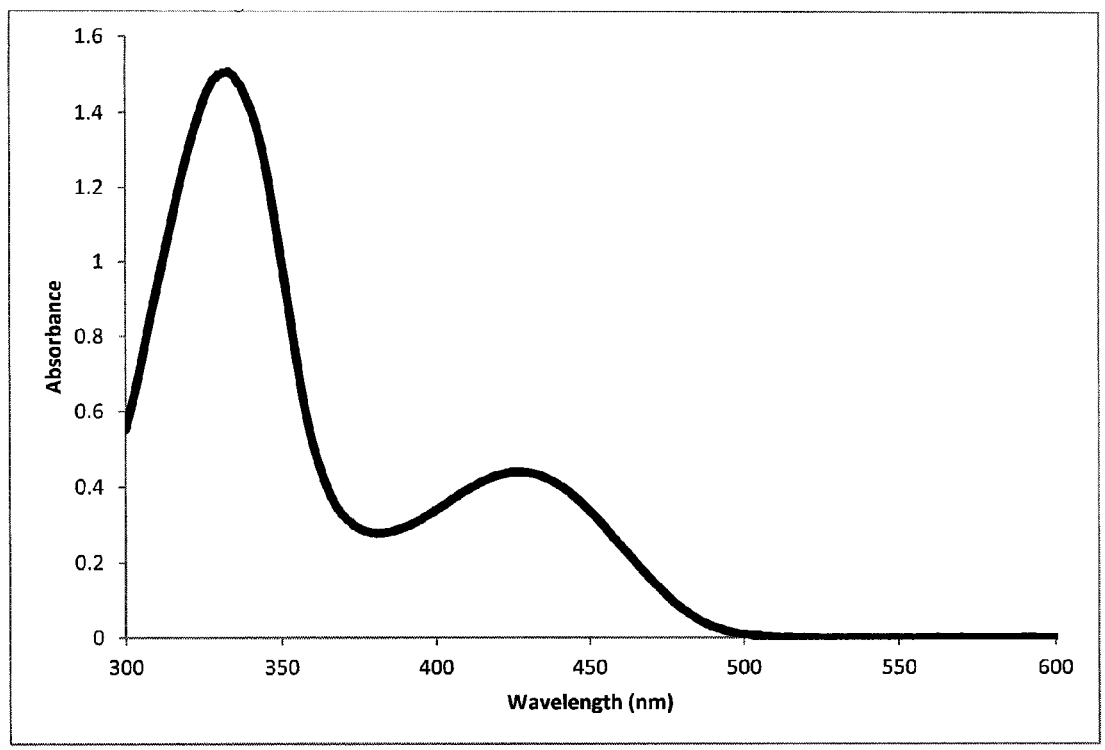
FIG. 9 is the UV-visible spectra in dichloromethane of BPh₂(BIAM).

The molecular structure is shown in FIG. 8. The UV-visible absorbance spectrum in dichloromethane is shown in FIG. 9.

PROPERTIES—These compounds exhibit metal-to-ligand charge transfer transitions (as has been reported for Re(CO)$_3$ diimine compounds), and the identity of the terminal atoms (nitrogen or oxygen) affects the absorption maximum. In one or more embodiments, UV-visible spectra show a red shift from 427 nm for the Re(CO)$_3$(BIAM)py complex to 512 nm for the Re(CO)$_3$(BOAM)py species.

Various modifications and alterations that do not depart from the scope and spirit of this invention will become apparent to those skilled in the art. This invention is not to be duly limited to the illustrative embodiments set forth herein.

What is claimed is:

1. A compound represented by the structure:

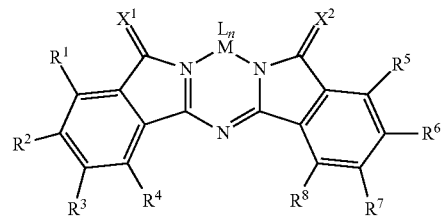

where M is selected from the group consisting of boron, gallium, phosphorus, rhenium, ruthenium, cobalt, and chromium, where each L is independently selected from ligands that form a coordination complex with M, where n is an integer from 0 to 4, X$^1$ and X$^2$ are independently selected from the group consisting of oxygen, sulfur, NR$^a$, and C(R$^b$)$_2$, wherein R$^a$ and each R$^b$ are independently selected from the group consisting of hydrogen, alkyl groups, and aryl groups, and where R$^1$, R$^2$, R$^3$, R$^4$, R$^5$, R$^6$, R$^7$, and R$^8$ are independently selected from the group consisting of C$_1$-C$_{30}$ alkyl, C$_1$-C$_{30}$ alkenyl, C$_1$-C$_{30}$ alkenyl, C$_1$-C$_{30}$ aryl, C$_1$-C$_{30}$ alkoxy, C$_1$-C$_{30}$ phenoxy, C$_1$-C$_{30}$ thioalkyl, C$_1$-C$_{30}$ thioaryl, C$_1$-C$_{30}$C(O)OR$^{11}$, N(R$^{12}$)(R$^{13}$), C(O)N(R$^{11}$)(R$^{12}$), F, Cl, Br, NO$_2$, CN, acyl, carboxylate, and hydroxyl moieties, and where R$^{11}$, R$^{12}$ and R$^{13}$ are independently selected from the group consisting of hydrogen, C$_1$-C$_{30}$ alkyl, and C$_1$-C$_{30}$ aryl moieties, or where two or more R groups, R$^1$-R$^8$, may together be a cyclic or heterocyclic moiety.

2. The compound of claim 1, wherein each L is independently selected from pyridine, N-methyl imidazole, and phenyl groups.

3. The compound of claim 1, wherein the compound is a bis(iminoisoindolinyl)azomethene complex with rhenium or boron.

4. The compound of claim 1, wherein the compound is a bis(oxoisoindolyl)azomethene complex with rhenium or boron.

5. A chromophoric chelate comprising a compound that is composed of two isoindoline moieties coordinated through the isoindolinyl nitrogen to a central atom, a bridging nitrogen atom that is covalently bonded to a carbon atom that is alpha to the isoindolinyl nitrogen in the 5-member ring of each isoindoline moiety, and a substituent that is doubly bonded to one or both of the alternate alpha carbons.

6. The compound of claim 5, wherein the central atom is an element that is capable of templating the formation of a chelate.

7. The compound of claim 6, wherein the substituent is selected from the group consisting of oxygen, sulfur, NR$^a$ and CR$^b$, where R$^a$ and each R$^b$ are independently selected from hydrogen, an alkyl group, and an aryl group.

8. The compound of claim 5, wherein the chelate further comprises ligands that are coordinated to the central atom and prevent the formation of a macrocycle.

9. A method for preparing a compound of claim 1, the method comprising the step of reacting ingredients including a metal-based or main group-based Lewis acid and an isoindoline having at least one imino group in an alpha position, in the presence of a Bronsted-Lowry base, and optionally in the presence of a solvent.

10. The method of claim 9, wherein the ingredients further include a second isoindoline having at least one imino group in an alpha position.

11. The method of claim 9, wherein the ingredients further include a coordinating ligand compound.

12. The method of claim 9, wherein the step of reacting occurs in the substantial absence of water.

13. The method of claim 9, wherein the step of reacting occurs in the presence of water.

14. The compound of claim 1, wherein M is rhenium or boron, each L is independently selected from pyridine groups, phenyl groups, and N-methyl imidazole groups, n is 1, $X^1$ and $X^2$ are each independently either oxygen or an imine group, and each $R^1$-$R^8$ is independently selected from the group consisting of hydrogen, alkyl groups, and cyano groups.

15. The compound of claim 1, wherein the compound is bis(iminoisoindolinyl)azomethene, bis(oxoisoindolinyl)azomethene, or a chelate thereof.

16. The method of claim 9, wherein the method may be represented by Scheme 2A or 2B below:

Scheme 2A

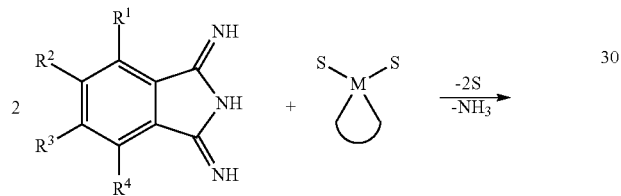

-continued

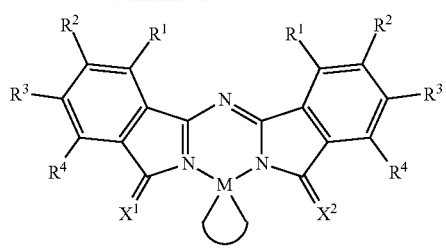

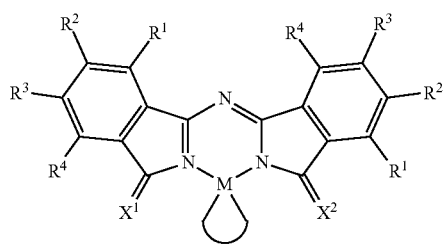

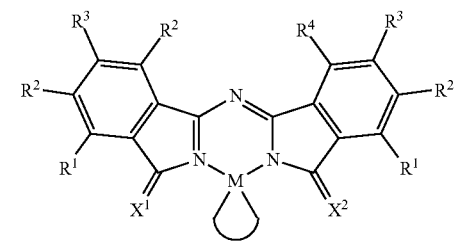

Scheme 2B

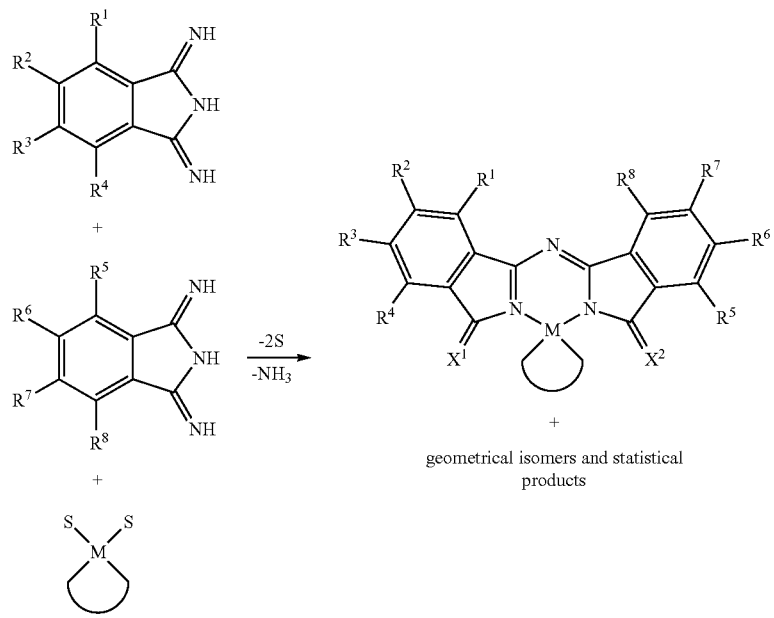

+ geometrical isomers and statistical products where each S is a labile group.

17. The method of claim 9, wherein the Lewis acid is selected from the group consisting of boron trifluoride, phenyl boronic acid, and pentacarbonylchlororhemium, triphenylboron.

18. The method of claim 17, wherein the isoindoline is a substituted or unsubstituted 1,3-diiminoisoindoline.

* * * * *